(12) United States Patent
Beveridge et al.

(10) Patent No.: US 8,552,185 B2
(45) Date of Patent: *Oct. 8, 2013

(54) PREPARATION OF AZOXYSTROBIN

(75) Inventors: Gillian Beveridge, Grangemouth (GB);
Ewan Campbell Boyd, Grangemouth
(GB); Jack Hugh Vass, Grangemouth
(GB); Alan John Whitton,
Grangemouth (GB)

(73) Assignee: Syngenta Limited, Guildford, Surrey (GB)

( * ) Notice: Subject to any disclaimer, the term of this patent is extended or adjusted under 35 U.S.C. 154(b) by 506 days.

This patent is subject to a terminal disclaimer.

(21) Appl. No.: 12/444,896

(22) PCT Filed: Oct. 2, 2007

(86) PCT No.: PCT/GB2007/003735
§ 371 (c)(1),
(2), (4) Date: Oct. 1, 2009

(87) PCT Pub. No.: WO2008/043978
PCT Pub. Date: Apr. 17, 2008

(65) Prior Publication Data
US 2010/0036124 A1 Feb. 11, 2010

(30) Foreign Application Priority Data
Oct. 9, 2006 (GB) .................................. 0619941.8

(51) Int. Cl.
*C07D 239/52* (2006.01)

(52) U.S. Cl.
USPC .......................................................... 544/319

(58) Field of Classification Search
USPC .......................................................... 544/319
See application file for complete search history.

(56) References Cited

U.S. PATENT DOCUMENTS

| 8,124,761 B2 * | 2/2012 | Whitton et al. ............... 544/319 |
| 2003/0092723 A1 * | 5/2003 | Weintritt et al. ............. 514/269 |

FOREIGN PATENT DOCUMENTS

| WO | 9208703 | 5/1992 |
| WO | 0172719 | 10/2001 |
| WO | 2006114572 | 11/2006 |

* cited by examiner

*Primary Examiner* — Deepak Rao
(74) *Attorney, Agent, or Firm* — R. Kody Jones

(57) ABSTRACT

The present invention relates, inter alia, to a process for preparing a compound of formula (I): using, as a catalyst 1,4-diazabicyclo[2.2.2]octane.

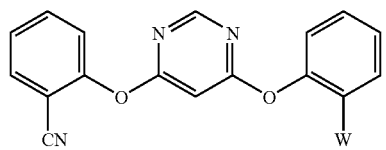

(I)

11 Claims, No Drawings

PREPARATION OF AZOXYSTROBIN

This application is a 371 of International Application No. PCT/GB2007/003735 filed Oct. 2, 2007, which claims priority to GB 0619941.8 filed Oct. 9, 2006, the contents of which are incorporated herein by reference.

The present invention relates to a process for preparing the strobilurin fungicide methyl (E)-2-{2-[6-(2-cyanophenoxy)pyrimidin-4-yloxy]phenyl}-3-methoxyacrylate (azoxystrobin).

Methods for preparing azoxystrobin are described in WO 92/08703. In one method, azoxystrobin is prepared by reacting 2-cyanophenol with methyl(E)-2-[2-(6-chloro-pyrimidin-4-yloxy)phenyl]-3-methoxyacrylate. A high-yielding method for producing asymmetrical 4,6-bis(aryloxy)pyrimidine derivatives is disclosed in WO 01/72719 in which a 6-chloro-4-aryloxypyrimidine is reacted with a phenol, optionally in the presence of a solvent and/or a base, with the addition of from 2 to 40 mol % of 1,4-diazabicyclo[2.2.2]octane (DABCO). In addition, it has previously been found by the present inventors that even lower concentrations of DABCO (for example, between 0.1 and 2 mol %) are also able to catalyse this reaction.

The present invention is based on the discovery that, when preparing azoxystrobin or an acetal precursor of azoxystrobin using DABCO as a catalyst, the order of addition of the reaction components has an effect on the yield and reaction rate.

Accordingly, the present invention provides a process for preparing a compound of formula (I):

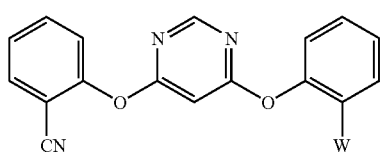

(I)

wherein W is the methyl(E)-2-(3-methoxy)acrylate group C(CO$_2$CH$_3$)=CHOCH$_3$ or the methyl 2-(3,3-dimethoxy)propanoate group C(CO$_2$CH$_3$)CH(OCH$_3$)$_2$, or a mixture of the two groups, which comprises either (a) reacting a compound of formula (II):

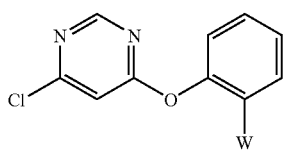

(II)

wherein W has the meaning given above, with 2-cyanophenol, or a salt thereof in the presence of between 0.1 and 40 mol % of DABCO, or (b) reacting the compound of formula (III):

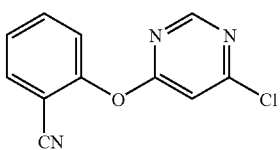

(III)

with a compound of formula (IV):

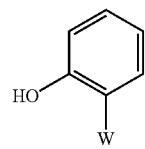

(IV)

or a salt thereof, where W has the meaning given above, in the presence of between 0.1 and 40 mol % of DABCO and wherein DABCO is not mixed with the compound of formula (II) to or the compound of formula (m) unless (i) 2-cyanophenol or the compound of formula (IV) or a salt of 2-cyanophenol or the compound of formula (IV) is present; or (ii) DABCO is present as an acid salt or (iii) conditions are such that DABCO and the compound of formula (II) or the compound of formula (E) are not able to react with each other; with the proviso that when between 0.1 and 2 mol % DABCO is used, the DABCO is not added last.

Conveniently, the process of the invention is carried out by mixing one of the components of the reaction, preferably in the presence of a solvent or diluent with the other component, if appropriate in the presence of a solvent or diluent. An acid acceptor is added at a convenient point, as discussed below, and the mixture is stirred, normally at an elevated temperature. After the reaction is judged to be complete, the reaction mixture is worked up and the product is isolated using conventional techniques well known to a skilled chemist. According to prior art methods, the DABCO catalyst may be added at any time to the reaction mixture including (i) as the first reactant, (ii) to the first component alone or (iii) after the second component has been added. However, it has now been found that, in order to promote higher product yields and a faster reaction rate, DABCO should not be allowed to react with the compound of formula (II) or the compound of formula (II) in the absence of 2-cyanophenol or the compound of formula (IV), or a salt of 2-cyanophenol or the compound of formula (IV). While not wanting to be bound by theory, it is believed that, in the absence of 2-cyanophenol or the compound of formula (IV), DABCO and the compounds of formula (II) or (III) react and then the reaction product can further convert to give a non-active species, thus reducing yield and available catalyst. It is also believed that the reaction between the neutral DABCO molecule and the compounds of formula (II) or (III) is inhibited in the presence of acid species. Therefore, if an acid salt of DABCO is added to the reaction flask or generated in situ (by the addition of neutral DABCO to a mixture containing an acid) and, provided that the acid acceptor is not present or not sufficiently soluble in the reaction mixture to quickly deprotonate the DABCO acid salt, the reaction between DABCO and the compounds of formula (II) or (III) is inhibited. It is also believed that, in the presence of 2-cyanophenol or the compound of formula (IV), the phenol can act as an acid source either protonating the DABCO salt directly or, after reaction between the phenol and the compounds of formula (II) or (III), may act as a base and be protonated by the mole of hydrochloric acid produced. Finally, in the presence of a salt of 2-cyanophenol or a salt of the compound of formula (IV), the reaction product of DABCO and the compounds of formula (II) or (III) reacts with the salt of 2-cyanophenol or the compound of formula (IV) to give the expected product of formula (I) and, concomitantly, regenerates the catalyst.

Thus, in particular, the process of the present invention may be carried out by, for example, any one of the following methods:

i) adding 2-cyanophenol or the compound of formula (IV) to the compound of formula (II) or the compound of formula (III), and then adding DABCO;

ii) adding 2-cyanophenol or the compound of formula (IV) to DABCO and then adding the compound of formula (II) or the compound of formula (III);

iii) adding DABCO to 2-cyanophenol or the compound of formula (IV) and then adding the compound of formula (II) or the compound of formula (II);

iv) adding the compound of formula (ID) or the compound of formula (D) to 2-cyanophenol or the compound of formula (IV) and then adding DABCO;

v) providing a mix of the compound of formula (II) or the compound of formula (III) with 2-cyanophenol or the compound of formula (IV) and then adding DABCO;

vi) providing a mix of DABCO with 2-cyanophenol or the compound of formula (IV) and then adding the compound of formula (II) or the compound of formula (m);

vii) adding a mix of 2-cyanophenol or the compound of formula (IV) and the compound of formula (II) or the compound of formula (III) to DABCO; or viii) adding a mix of 2-cyanophenol or the compound of formula (IV) and DABCO to the compound of formula (II) or the compound of formula (In);

ix) adding DABCO to an acidic solution of the compound of formula (II) or the compound of formula (m) in which sufficient acid is present to convert all of the DABCO to a salt, and then adding 2-cyanophenol or the compound of formula (IV) provided that the acid acceptor is either not added before the 2-cyanophenol or the reaction between the DABCO salt and the acid acceptor is slow; or I x) mixing an acid salt of DABCO, either as a solid or a preformed salt by the reaction of acid and DABCO, to the compound of formula (E) or the compound of formula (III) and then adding 2-cyanophenol or the compound of formula (IV) provided that the base is either not added before the 2-cyanophenol or the reaction between the DABCO salt and the acid acceptor is slow.

Suitable acid salts of DABCO include, but are not limited to DABCOH$^+$Cl$^-$, DABCOH$^+$(HSO$_4$)$^-$, (DABCOH$^+$)$_2$SO$_4^{2-}$ and DABCOH$^+$(SO$_3$Me)$^-$.

Of course, if DABCO is not able to react with the compound of formula (II) or the compound or formula (III), for example, if both components are in a solid state or if one component is insoluble (or perhaps only partially soluble) in the solvent/diluent used in the reaction, then they can be mixed with impunity. However, in such a case, before the conditions are made suitable for the reaction to take place, 2-cyanophenol or the compound of formula (IV), or a salt of 2-cyanophenol or the compound of formula (IV) must be added.

Further mixing options are thus allowed if the components of the reaction are first mixed in conditions under which they are not able to react. For example, a mix of the compound of formula (II) or the compound of formula (E) with DABCO may be provided and the reaction not started until 2-cyanophenol or the compound of formula (IV) is added.

In a particular embodiment, the process of invention comprises reacting a compound of formula (II):

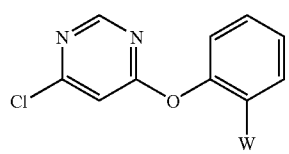

(II)

wherein W has the meaning given above, with 2-cyanophenol, or a salt thereof (suitably potassium 2-cyanophenoxide) in the presence of between 0.1 and 40 mol % of DABCO.

When the process of the invention is carried out using a compound of formula (II) where W is the methyl 2-(3,3-dimethoxy)propanoate group or using a compound of formula (IV) where W is the methyl 2-(3,3-dimethoxy)propanoate group, the product obtained may include a proportion of the compound of formula (I) where W is the methyl(E)-2-(3-methoxy)acrylate group. This may happen because it is possible that methanol is eliminated from the methyl 2-(3,3-dimethoxy)propanoate group under the conditions of the process. For the same reason, if the process is carried out using a compound of formula (II) or a compound of formula (IV) where W is a mixture of the methyl 2-(3,3-dimethoxy)propanoate group and the methyl(E)-2-(3-methoxy)acrylate group (and the invention includes such a process), the product obtained will be a compound of formula (I) where W is a mixture of the methyl 2-(3,3-dimethoxy)propanoate group and the methyl(E)-2-(3-methoxy)acrylate group; however, the product may have a higher proportion of the compound of formula (I) where W is the methyl(E)-2-(3-methoxy)acrylate group than expected from the proportion of (E)-2-(3-methoxy)acrylate group in the mixed starting material due to this potential elimination of methanol. This is of no real consequence because it will normally be required to convert the product of formula (I) where W is the methyl 2-(3,3-dimethoxy)propanoate group to the compound of formula (I) where W is the group methyl(E)-2-(3-methoxy)acrylate group by the elimination of methanol.

Conveniently the process of the invention is carried out in a suitable inert solvent or diluent. These include, for example, aliphatic, alicyclic and aromatic hydrocarbons, such as petroleum ether, hexane, heptane, cyclohexane, methylcyclohexane, benzene, toluene, xylene and decalin; halogenated hydrocarbons, such as chlorobenzene, dichlorobenzene, dichloromethane, chloroform, carbon tetrachloride, dichloroethane and trichloroethane; heteroaromatic solvents such as pyridine or a substituted pyridine, for example, 2,6-dimethylpyridine; ethers, such as diethyl ether, diisopropylether, methyl-tert-butyl ether, methyl-tert-amyl ether, dioxane, tetrahydrofuran, 1,2-dimethoxyethane, 1,2-diethoxyethane and anisole; ketones, such as acetone, butanone, methyl isobutyl ketone and cyclohexanone; nitriles, such as acetonitrile, propionitrile, n- and i-butyronitrile and benzonitrile; amides, such as N,N-dimethylformamide, N,N-dimethylacetamide, N-methylformamide, N-methyl-pyrrolidone and hexamethylphosphoric triamide; tertiary amines, in particular, amines of the formula R$^1$R$^2$R$^3$N where R$^1$, R$^2$ and R$^3$ are each independently C$_{1-10}$ (especially C$_{1-8}$) alkyl, C$_{3-6}$ cycloalkyl, aryl (especially phenyl) or aryl(C$_{1-4}$)alkyl (especially benzyl); or two or three of R$^1$, R$^2$ and R$^3$ join together with the nitrogen atom to which they are attached to form one, two or three 5-, 6- or 7-membered alicyclic rings optionally fused and optionally containing a second ring nitrogen atom, examples of suitable tertiary amines being N,N-di-isopropylethylamine (Hünig's base), N,N-dimethylaniline, triethylamine, t-butyldimethyl-amine, N,N-diisopropylmethylamine, N,N-diisopropylisobutylamine, N,N-diisopropyl-2-ethylbutylamine, tri-n-butylamine, N,N-dicyclohexylmethylamine, N,N-dicyclohexylethyl-amine, N-tert-butylcyclohexylamine, N,N-dimethylcyclohexylamine, 1,5-diazabicyclo[4.3.0]-non-5-ene, 1,8-diazabicyclo[5.4.0]undec-7-ene or 2-dimethylaminopyridine; esters, such as methyl acetate, ethyl acetate and isopropyl acetate; sulphoxides, such as dimethylsulphoxide; sulphones, such as dimethylsulphone or sulpholane; and mixtures of such solvents and diluents and mixtures of one or more of them with water. In addition, if the starting compounds for the reaction or the product from the reaction are in the form of liquids or will be liquid at the reaction temperature, they may act as diluent/solvent for the process of the invention. In such a situation, additional diluent or solvent may not be required.

Particularly suitable diluents are ketones [such as methyl isobutyl ketone and cyclohexanone], esters [such as isopropyl acetate], tertiary amines [such as [N,N-di-isopropylethylamine (Hünig's base)], aromatic hydrocarbons [such as toluene or xylene (mixed isomers or single isomer)] and amides [such as N,N-dimethylformamide]. In a particular aspect of the present invention, methyl isobutyl ketone is used as diluent. In a further aspect of the present invention, cyclohexanone is used as diluent. In a further aspect of the present invention, isopropyl acetate is used as diluent. In a further aspect of the present invention, N,N-dimethylformamide is used as diluent. In a further aspect of the present invention, toluene is used as diluent. In a further aspect of the present invention, N,N-diisopropylethylamine (Hünig's base) is used as diluent. Most suitably, the diluent used in the present invention is N,N-dimethylformamide.

In a further embodiment of the present invention, the process is carried out in an aqueous organic solvent system. Suitably, in this embodiment, when the compound of formula (II) is reacted with 2-cyanophenol, the 2-cyanophenol is present as a salt. This salt may either have been added as is or be generated in situ from the neutral phenol and the acid acceptor (see below). Suitably, the salt is a lithium, caesium, sodium, potassium, 1,5-diazabicyclo[4.3.0]-non-5-ene or 1,8-diazabicyclo[5.4.0]undec-7-ene salt of 2-cyanophenol. More suitably, the salt is the 1,8-diazabicyclo[5.4.0]undec-7-ene, sodium or potassium salt of 2-cyanophenol. Even more suitably, the salt is the sodium or potassium salt of 2-cyanophenol. Most suitably, the salt is potassium 2-cyanophenoxide. Suitable co-solvents for use in such an aqueous process are solvents which are at least partially water immiscible solvents such as cyclohexanone, methyl isobutyl ketone and isopropyl acetate. Advantageously, the water is removed throughout the reaction when these partially water immiscible solvents are used. In addition, it has also been found that water miscible solvents may also be used in such an aqueous process. Suitable water miscible solvents are N,N-dimethylformamide, N,N-dimethylacetamide, N-methylpyrrolidinone and dimethyl sulphoxide. In one embodiment, the water is removed throughout the reaction when the water miscible solvents are used. Most suitably, when such aqueous systems are used, the salt of 2-cyanophenol is potassium 2-cyanophenoxide and the diluent is cyclohexanone, methyl isobutyl ketone, isopropyl acetate or N,N-dimethylformamide. It is noted that when the 2-cyanophenol is added to the process as an aqueous solution of potassium 2-cyanophenoxide it is possible to reduce the quantity of acid acceptor (see below) used.

In addition, the process of the invention is preferably carried out in the presence of at least 0.8 moles of an acid acceptor per mole of 2-cyanophenol or a compound of formula (IV). Suitable acid acceptors are all customary inorganic and organic bases. These include, for example, alkaline earth metal and alkali metal hydroxides, acetates, carbonates, bicarbonates, phosphates, hydrogen phosphates and hydrides [such as sodium hydroxide, potassium hydroxide, sodium acetate, potassium acetate, sodium carbonate, potassium carbonate, sodium bicarbonate, potassium bicarbonate, potassium phosphate, potassium hydrogen phosphate, sodium phosphate, potassium hydrogen phosphate, calcium hydride, sodium hydride and potassium hydride], guanidines, phosphazines (see, for example, Liebigs Ann. 1996, 1055-1081), prophosphatranes (see, for example, JACS 1990, 9421-9422), metal dialkylamines [such as lithium di-iso-propylamide] and tertiary amines [such as those described above as possible solvents or diluents]. Particularly suitable acid acceptors are the alkaline earth metal and alkali metal carbonates, especially potassium carbonate and sodium carbonate and 1,5-diazabicyclo[4.3.0]non-5-ene and 1,8-diazabicyclo[5.4.0]undec-7-ene. More suitably, the acid acceptor is potassium carbonate. Most suitably, the present invention is carried out in the presence of methyl isobutyl ketone, cyclohexanone, isopropyl acetate, N,N-diisopropylethylamine (Hünig's base) or N,N-dimethylformamide with potassium carbonate as the acid acceptor.

The time at which the acid acceptor is added may be important in some embodiments of the invention. If the acid acceptor to be used is not added as an aqueous solution and will not generate large (one mole of water per mole of phenol deprotonated) amounts of water, such as 1,5-diazabicyclo[4.3.0]non-5-ene, 1,8-diazabicyclo[5.4.0]undec-7-ene, alkali metal phosphate or hydrogen phosphate, greater than mole of alkali metal or alkaline earth carbonate, then the acid acceptor can be added at any time in the process. Also, if the 2-cyanophenol is the first reaction component added, any acid acceptor can be added at any time and consideration of whether to remove any water generated by the 2-cyanophenol plus acid acceptor reaction can be made. Where a compound of formula (II) is charged first, aqueous solutions of acid acceptors should not be added before the 2-cyanophenol is added to the mixture. For a compound of formula (IV) added first, preferably in the presence of a diluent, it is advantageous to add the compound of formula (III) before adding the acid acceptor. For a compound of formula (II) added first, preferably in the presence of a diluent, the acid acceptor can be added at any suitable time. While not wanting to be bound by theory, strong bases in the presence of significant quantities of water can hydrolyse compounds of formula (II) resulting in by-product formation and lower yields—the presence of 2-cyanophenol or both components of the reaction will neutralise the strong bases and allow the desired reaction to occur. Obviously, in selecting the amount of acid acceptor to be added, consideration of effects of potential excesses of acid acceptors should be made and normally, when using aqueous solutions of acid acceptors, or acid acceptor which generate a mole of water per mole of phenol deprotonated such as alkali or alkaline earth metal hydroxides or hydrogen carbonates, close to stoichiometric quantities of base should be used.

The process of the invention is carried out in the presence of between 0.1 and 40 mol % of 1,4-diazabicyclo[2.2.2]octane (DABCO). Suitably, it is carried out in the presence of between 0.2 and 40 mol % of DABCO. More suitably, it is carried out in the presence of between 0.5 and 10 mol %. Most suitably, it is carried out in the presence of between 0.5 and 5 mol % DABCO.

In a particular embodiment of the invention the process is carried out in the presence of about 1 mol % DABCO with methyl isobutyl ketone, cyclohexanone, isopropyl acetate, N,N-di-isopropylethylamine (Hünig's base), toluene, or N,N-dimethylformamide as diluent. More suitably, the diluent is N,N-dimethylformanide or isopropyl acetate. Most suitably, the diluent is N,N-dimethylformamide. Suitably, the acid acceptor will be potassium carbonate.

When carrying out the process of the invention, the reaction temperature can be varied within a relatively wide range. The temperature chosen will depend on the nature of the solvent or diluent, for example on its boiling point and/or its effectiveness for promoting the desired reaction, and on the rate at which the reaction is to be carried out. In any given solvent or diluent, the reaction will tend to progress more slowly at lower temperatures. In general, the reaction may be carried out at a temperature of from 0 to 120° C., suitably at a temperature of from 40 to 100° C., and typically at a temperature of from 45 to 95° C., for example, from 60 to 95° C.

The process of the invention can be carried out at any reasonable pressure depending on the solvent, base and reaction temperature. For low boiling diluents or reagents, higher temperatures can be accessed at higher than atmospheric pressures, and reactions can be carried out at atmospheric pressures or under vacuum if desired. Suitably, the reaction may be carried out at a pressure of from 0.01 to 10 Bara, more suitably at a pressure of from 0.5 to 5 Bara and most suitable at a pressure of from 0.8 to 2 Bara, for example at ambient pressure.

For carrying out the process of the invention, suitably from 0.4 to 4 mol, more suitably from 0.95 to 1.5 mol and most suitably from 1 to 1.2 mol, of 2-cyanophenol is employed per mol of a compound of formula (II); and similar amounts (0.4 to 4 mol, more suitably from 0.95 to 1.5 mol and most suitably from 1 to 1.2 mol) of a compound of formula (IV) are employed per mole of the compound of formula (m).

2-Cyanophenol is a commercially available material.

The compound of formula (II), where W is the methyl(E)-2-(3-methoxy)acrylate group $C(CO_2CH_3)=CHOCH_3$, and the compound of formula (II) where W is the methyl 2-(3,3-dimethoxy)propanoate group $C(CO_2CH_3)CH(OCH_3)_2$, may be prepared as described in WO 92/08703 from the reaction of 3-(α-methoxy)methylenebenzofuran-2(3H)-one (derived from benzofuran-2(31H)-one) with 4,6-dichloropyrimidine. The compound of formula (II), where W is the methyl(E)-2-(3-methoxy)acrylate group, may also be prepared by eliminating methanol from (that is, by the demethanolysis of) the compound of formula (II) where W is the methyl 2-(3,3-dimethoxy)propanoate group, as described in WO 92/08703 or WO 98/07707. The compound of formula (II), where W is the methyl 2-(3,3-dimethoxy)propanoate group, may be prepared as described in GB-A-2291874 by reacting a compound of formula (IV), where W is the methyl 2-(3,3-dimethoxy)propanoate group, with 4,6-dichloropyrimidine. It may be purified before use by known techniques or may be used in an unpurified state from a previous reaction, for example, in a 'one-pot' reaction.

The compound of formula (IV), where W is the methyl 2-(3,3-dimethoxy)propanoate group, may be prepared as described in GB-A-2291874 from 3-(α-methoxy)methylenebenzofuran-2(3H)-one. The compound of formula (IV), where W is the methyl(E)-2-(3-methoxy)acrylate group, may be prepared by the procedure described in EP 0 242 081 or by the demethanolysis of the compound of formula (IV) where W is the methyl 2-(3,3-dimethoxy)propanoate group. In this case, the phenolic group needs to be protected by, for example, benzylation before demethanolysis and then de-protected afterwards.

The following Examples illustrate the invention. The examples are not intended as necessarily representative of the overall testing performed and are not intended to limit the invention in any way.

EXAMPLES

In these examples:
DABCO=diazabicylclo[2.2.2]octane
MIBK=methylisobutylketone
DMF=N,N-dimethylformamide
DBU=1,8-diazabicyclo[5.4.0]undec-7-ene a) Conversion of methyl(E)-2-{2-[6-chloropyrimidin-4-yloxy]phenyl}-3-methoxyacrylate to methyl (E)-2-{2-[6-(2-cyanophenoxy)pyrimidin-4-yloxy]phenyl}-3-methoxyacrylate with DABCO (2.6 mol %) added before the 2-cyanophenol To a stirred solution of methyl(E)-2-{2-[6-chloropyrimidin-4-yloxy]phenyl}-3-methoxyacrylate in DMF (207.3 g at 46.4%, 0.3 mols) at 50° C., was added potassium carbonate (63.5 g at 98%, 0.45 mols) and DABCO (0.89 g at 98%, 0.0078 mols, 2.6 mol %). The mixture was allowed to stir for 5 minutes and then a solution of 2-cyanophenol in DMF (78.5 g at 50%, 0.33 mols) was added. The mixture was heated to 65° C. and held at that temperature for 1 hour. The DMF was removed by vacuum distillation and then the residues were dissolved in toluene (165.8 g), heated to 80° C. and washed with water (318.6 g). The toluene solution (301.7 g) contained methyl(E)-2-{2-[6-(2-cyanophenoxy)pyrimidin-4-yloxy]phenyl}-3-methoxyacrylate (37.0% w/w), 92% of theory.

b) Conversion of methyl(E)-2-{2-[6-chloropyrimidin-4-yloxy]phenyl}-3-methoxyacrylate to methyl (E)-2-[2-{6-(2-cyanophenoxy)pyrimidin-4-yloxy] phenyl}-3-methoxyacrylate with DABCO (2.6 mol %) added after the 2-cyanophenol To a stirred solution of methyl(E)-2-{2-[6-chloropyrimidin-4-yloxy]phenyl}-3-methoxyacrylate in DMF (207.3 g at 46.4%, 0.3 mols) at 48° C., was added potassium carbonate (54.1 g at 98%, 0.38 mols), and a solution of 2-cyanophenol in DMF (78.5 g at 50%, 0.33 mols). DABCO (0.89 g at 98%, 0.0078 mols, 2.6 mol %) was added and the mixture heated to 65° C. and held at that temperature for 1 hour. The DMF was removed by vacuum distillation and then the residues were dissolved in toluene (165.8 g), heated to 80° C. and washed with water (318.6 g). The concentration of methyl(E)-2-{2-[6-(2-cyanophenoxy)pyrimidin-4-yloxy]phenyl}-3-methoxyacrylate in the toluene solution was 39.1% w/w (98.6% of theory).

c) Conversion of methyl(E)-2-{2-[6-chloropyrimidin-4-yloxy]phenyl}-3-methoxyacrylate to methyl (E)-2-{2-[6-(2-cyanophenoxy)pyrimidin-4-yloxy] phenyl}-3-methoxyacrylate with DABCO (2.6 mol %) added after the 2-cyanophenol To a stirred solution of methyl(E)-2-{2-[6-chloropyrimidin-4-yloxy]phenyl}-3-methoxyacrylate in DMF (207.3 g at 46.4%, 0.3 mols) at 48° C., was added potassium carbonate (54.1 g at 98%, 0.38 mols) and a solution of 2-cyanophenol in DMF (78.5 g at 50%, 0.33 mols). DABCO (0.89 g at 98% w/w, 0.0078 mols, 2.6 mol %) was added and the mixture heated to 65° C. and held at that temperature for 1 hour. The DMF was removed by vacuum distillation, to a final temperature of 100° C. and then the residues were dissolved, while still hot, in toluene (165.8 g). Hot water (319 g) was added and the mixture stirred at 80° C. for 30 minutes before settling and separating the aqueous phase. The concentration of methyl (h)-2-{2-[6-(2-cyanophenoxy)pyrimidin-4-yloxy]phenyl}-3-methoxyacrylate in the toluene solution (306.7 g) was 39.3% w/w (99.7% of theory).

d) Conversion of methyl(E)-2-{2-[6-chloropyrimidin-4-yloxy]phenyl}-3-methoxyacrylate to methyl (E)-2-{2-[6-(2-cyanophenoxy)pyrimidin-4-yloxy]phenyl}-3-methoxy acrylate with DABCO (2.6 mol %) added after the 2-cyanophenol To a stirred solution of methyl(E)-2-{2-[6-chloropyrimidin-4-yloxy]phenyl}-3-methoxyacrylate in DMF (207.3 g at 46.4%, 0.3 mols) at 48° C., was added potassium carbonate (54.1 g at 98%, 0.38 mols) and a solution of 2-cyanophenol in DMF (78.5 g at 50% w/w, 0.33 mols). DABCO (0.89 g at 98% w/w, 0.0078 mols, 2.6 mol %) was added and the mixture heated to 65° C. and held at that temperature for 1 hour. The DMF was removed by vacuum distillation, to a final temperature of 100° C. and then the residues were dissolved, while still hot, in toluene (165.8 g). Hot water (319 g) was added and the mixture stirred at 80° C. for 30 minutes before settling and separating the aqueous phase. The concentration of methyl (E)-2-{2-[6-(2-cyanophenoxy)pyrimidin-4-yloxy]phenyl}-3-methoxyacrylate in the toluene solution (303.9 g) was 39.1% w/w (98.3% of theory).

e) Coupling of methyl(E)-2-{2-[6-chloropyrimidin-4-yloxy]phenyl}-3-methoxyacrylate with 2-cyanophenol in MIBK with 2 mol % DABCO added after the 2-cyanophenol A slurry containing methyl(E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenol (33.6 g at 97.5%, 0.275 mols) in MIBK (160 mls) was heated to approximately 60° C. A solution of DABCO (0.56 g, 0.005 mols) in MIBK (10 mls) was added. The mixture was heated to 80° C. and held at this temperature for 200 minutes. Water (300 mls) was charged to the reaction, maintaining the temperature in the range 70-80° C. The mixture was stirred for 40 minutes then settled and the lower aqueous phase separated. The MIBK solution (238.6 g) contained methyl(E)-2-{2-[6-(2-cyanophenoxy)pyrimidin-4-yloxy]phenyl}-3-methoxyacrylate (41.3% w/w) 97.8% of theory.

f) Coupling of methyl(E)-2-{2-[6-chloropyrimidin-4-yloxy]phenyl}-3-methoxyacrylate with 2-cyanophenol in MIBK with 2 mol % DABCO added before the 2-cyanophenol To a slurry containing methyl(E)-2-{2-[6-chloropyrimidin-4-yloxy]phenyl}-3-methoxyacrylate (80.9 g at 99%, 0.25 mols) and potassium carbonate (52.8 g at 98%, 0.375 mols) in MIBK (160 mls) was added a solution of DABCO (0.56 g, 0.005 mols) in MIBK (10 mls). The mixture was heated to approximately 60° C. and then 2-cyanophenol (33.6 g at 97.5%, 0.275 mols) was charged. The mixture was heated to 80° C. and held at this temperature for 280 minutes. Water (300 mls) was charged to the reaction, maintaining the temperature in the range 70-80° C. The mixture was stirred for 40 minutes then settled and the lower aqueous phase separated.

The MIBK solution (237.0 g) contained methyl(E)-2-{2-[6-(2-cyanophenoxy)pyrimidin-4-yloxy]phenyl}-3-methoxyacrylate (40.2% w/w) 94.5% of theory.

g) Coupling of methyl(E)-2-{2-[6-chloropyrimidin-4-yloxy]phenyl}-3-methoxyacrylate with 2-cyanophenol in DMF with 5.0 mol % DABCO added after 2-cyanophenol A stirred solution of methyl(E)-2-{2-[6-chloropyrimidin-4-yloxy]phenyl}-3-methoxyacrylate (80.0 g at 98.0% w/w, 0.245 mols) in DMF (80 g) was heated to 60° C. Potassium carbonate (52.4 g at 98% w/w, 0.37 mols), a solution of 2-cyanophenol (33.3 g at 97.5% w/w, 0.27 mols) in DMF (33.3 g), and DABCO (1.43 g at 97% w/w, 0.012 mols) were added, with a 5 minute interval between each addition. The mixture was heated to 80° C. (exotherm raised temperature to 89° C.). The reaction was complete in 10 minutes. The DMF was removed from the mixture by vacuum distillation to a maximum temperature of 100° C. After allowing the distillation residues to cool slightly, toluene (137 g) was added. The solution was stirred at 75-80° C. for 5 minutes and then hot water (263.6 g) was added, keeping the temperature of the mixture above 70° C. The two phase mixture was stirred at 80° C. for 30 minutes, then settled and separated. The toluene solution (229.7 g) contained methyl(E)-2-{2-[6-(2-cyanophenoxy)pyrimidin-4-yloxy]phenyl}-3-methoxyacrylate (42.0% w/w), 98.0% of theory.

h) Coupling of methyl(E)-2-{2-[6-chloropyrimidin-4-yloxy]phenyl}-3-methoxyacrylate with 2-cyanophenol in DMF with 5.0 mol % DABCO added before 2-cyanophenol A stirred solution of methyl(E)-2-{2-[6-chloropyrimidin-4-yloxy]phenyl}-3-methoxyacrylate (80.0 g at 98.0% w/w, 0.245 mols) in DMF (80 g) was heated to 60° C. Potassium carbonate (52.4 g at 98% w/w, 0.37 mols), DABCO (1.43 g at 97% w/w, 0.012 mols), and a solution of 2-cyanophenol (33.3 g at 97.5% w/w, 0.27 mols) in DMF (33.3 g) were added, with a 5 minute interval between each addition. The mixture was heated to 80° C. The reaction was complete after 360 minutes. The DMF was removed from the mixture by vacuum distillation to a maximum temperature of 100° C. After allowing the distillation residues to cool slightly, toluene (137 g) was added. The solution was stirred at 75-80° C. for 5 minutes and then hot water (263.6 g) was added, keeping the mixture temperature above 70° C. The two phase mixture was stirred at 80° C. for 30 minutes, then settled and separated. The toluene solution (228.9 g) contained methyl(E)-2-{2-[6-(2-cyanophenoxy)pyrimidin-4-yloxy]phenyl}-3-methoxyacrylate (37%% w/w), 86.1% of theory.

i) Coupling of methyl(E)-2-{2-[6-chloropyrimidin-4-yloxy]phenyl}-3-methoxyacrylate with 2-cyanophenol in DMF with 5.0 mol % DABCO added after 2-cyanophenol and potassium carbonate added last A stirred solution of methyl(E)-2-{2-[6-chloropyrimidin-4-yloxy]phenyl}-3-methoxyacrylate (80.0 g at 98.0% w/w, 0.245 mols) in DMF (80 g) was heated to 60° C. A solution of 2-cyanophenol (33.3 g at 97.5% w/w, 0.27 mols) in DMF (33.3 g), DABCO (1.43 g at 97% w/w, 0.012 mols) and potassium carbonate (52.4 g at 98% w/w, 0.37 mols) were added, with a 5 minute interval between each addition. The mixture was heated to 80° C. (exotherm raised temperature to 89° C.). The reaction was complete in approximately 10 minutes. The DMF was removed from the mixture by vacuum distillation to a maximum temperature of 100° C. After allowing the distillation residues to cool slightly, toluene (137 g) was added. The solution was stirred at 75-80° C. for 5 minutes and then hot water (263.6 g) was added, keeping the mixture temperature above 70° C. The two phase mixture was stirred at 80° C. for 30 minutes, then settled and separated. The toluene solution (229.1 g) contained methyl(E)-2-{2-[6-(2-cyanophenoxy)pyrimidin-4-yloxy]phenyl}-3-methoxyacrylate (41.7% w/w), 97.1% of theory.

j) Coupling of methyl(E)-2-{2-[6-chloropyrimidin-4-yloxy]phenyl}-3-methoxyacrylate with 2-cyanophenol in DMF with 5.0 mol % DABCO added before 2-cyanophenol. Methyl(E)-2-{2-[6-chloropyrimidin-4-yloxy]phenyl}-3-methoxyacrylate was added last A stirred suspension of potassium carbonate (51.6 g at 98% w/w, 0.37 mols) and DMF (80 g) was heated to 60° C. DABCO (1.41 g at 97% w/w, 0.012 mols), a solution of 2-cyanophenol (32.8 g at 97.5% w/w, 0.27 mols) in DMF (32.8 g), and methyl(E)-2-{2-[6-chloropyrimidin-4-yloxy]phenyl}-3-methoxyacrylate (80.0 g at 98.0% w/w, 0.244 mols) were added, with a 5 minute interval between each addition. The mixture was heated to 80° C. (exotherm raised temperature to 84° C.). The reaction was complete in approximately 20 minutes. The DMF was removed from the mixture by vacuum distillation to a maximum temperature of 100° C. After allowing the distillation residues to cool slightly, toluene (134.8 g) was added. The solution was stirred at 75-80° C. for 5 minutes and then hot water (259.4 g) was added, keeping the mixture temperature above 70° C. The two phase mixture was stirred at 80° C. for 30 minutes, then settled and separated. The toluene solution (225.6 g) contained methyl(E)-2-{2-[6-(2-cyanophenoxy)pyrimidin-4-yloxy]phenyl}-3-methoxyacrylate (43.79% w/w), 100% of theory.

k) Coupling of methyl(E)-2-{2-[6-chloropyrimidin-4-yloxy]phenyl}-3-methoxyacrylate with 2-cyanophenol in DMF with 5.0 mol % DABCO added before 2-cyanophenol. Potassium carbonate was added last A stirred solution of methyl(E)-2-{2-[6-chloropyrimidin-4-yloxy]phenyl}-3-methoxyacrylate (80.0 g at 98.0% w/w, 0.244 mols) in DMF (80 g) was heated to 60° C. DABCO (1.41 g at 97% w/w, 0.012 mols), a solution of 2-cyanophenol (32.8 g at 97.5% w/w, 0.27 mols) in DMF (32.8 g) and potassium carbonate (51.6 g at 98% w/w, 0.37 mols) were added, with a 5 minute interval between each addition. The mixture was heated to 80° C. The reaction was complete in 4 hours. The DMF was removed from the mixture by vacuum distillation to a maximum temperature of 100° C. After allowing the distillation residues to cool slightly, toluene (134.8 g) was added. The solution was stirred at 75-80° C. for 5 minutes and then hot water (259.4 g) was added, keeping the mixture temperature above 70° C. The two phase mixture was stirred at 80° C. for 30 minutes, then settled and separated. The toluene solution (226.6 g) contained methyl(E)-2-{2-[6-(2-cyanophenoxy)pyrimidin-4-yloxy]phenyl}-3-methoxyacrylate (37.95% w/w), 87.4% of theory.

l) Coupling of methyl(E)-2-{2-[6-chloropyrimidin-4-yloxy]phenyl}-3-methoxyacrylate with 2-cyanophenol in isopropyl acetate with 40.0 mol % DABCO added after 2-cyanophenol To isopropyl acetate (20.6 g) at 40° C. was added methyl (E)-2-{2-[6-chloropyrimidin-4-yloxy]phenyl}-3-methoxyacrylate (32.8 g at 98% w/w, 0.1 mols). After stirring for 10 minutes potassium carbonate (14.1 g at 98% w/w, 0.1 mols) was added. Further isopropyl acetate (0.8 g) was added (to mobilise the slurry). After stirring for a further 10 minutes at 40° C., 2-cyanophenol (12.2 g at 97.5% w/w, 0.1 mols) was added. 10 minutes later DABCO (4.61 g at 97% w/w, 0.04 mols) was added. The mixture was stirred at 40° C. (exotherm took the temperature to 45° C.). The reaction was complete after 30 minutes. The reaction mixture was heated to 60° C. and diluted with isopropyl acetate (13.7 g) and toluene (24.5 g). The temperature was raised to 65° C. and then hot water (106.2 g) was added. The two phase mixture was stirred at 75° C. for 30 minutes and then settled and separated. The organic phase (107.6 g) contained methyl(E)-2-{2-[6-(2-cyanophenoxy)pyrimidin-4-yloxy]phenyl}-3-methoxyacrylate (36.5% w/w), 97.5% of theory.

m) Coupling of methyl(E)-2-{2-[6-chloropyrimidin-4-yloxy]phenyl}-3-methoxyacrylate with 2-cyanophenol in isopropyl acetate with 40.0 mol % DABCO added before 2-cyanophenol To isopropyl acetate (20.6 g) at 40° C., was added methyl (E)-2-{2-[6-chloropyrimidin-4-yloxy]phenyl}-3-methoxyacrylate (32.8 g at 98% w/w, 0.1 mols). After stirring for 10 minutes potassium carbonate (14.1 g at 98% w/w, 0.1 mols) was added along with a further charge of isopropyl acetate (0.8 g). After stirring for a further 10 minutes at 40° C., DABCO (4.61 g at 97% w/w, 0.04 mols) was added and then, after 10 minutes, 2-cyanophenol (12.2 g at 97.5% w/w, 0.1 mols) was charged. The mixture was stirred at 40° C. (exotherm took the temperature to 45° C.). The reaction was complete after approximately 20-30 minutes. Isopropyl acetate (13.7 g) and toluene (24.5 g) were added and the mixture heated to 60-65° C. before charging hot water (106.2 g). The two phase mixture was stirred at 75° C. for 30 minutes and then settled and separated. The organic phase (94.7 g) contained methyl(E)-2-{2-[6-(2-cyanophenoxy)pyrimidin-4-yloxy]phenyl}-3-methoxyacrylate (40.2% w/w), 94.5% of theory.

n) Coupling of methyl(E)-2-{2-[6-chloropyrimidin-4-yloxy]phenyl}-3-methoxyacrylate with 2-cyanophenol in isopropyl acetate with 40.0 mol % DABCO and extra solvent added before 2-cyanophenol To isopropyl acetate (20.6 g) at 40° C., was added methyl (E)-2-{2-[6-chloropyrimidin-4-yloxy]phenyl}-3-methoxyacrylate (32.8 g at 98% w/w, 0.1 mols). After stirring for 10 minutes potassium carbonate (14.1 g at 98% w/w, 0.1 mols) was added along with a further charge of isopropyl acetate (0.8 g). After stirring for a further 10 minutes at 40° C., DABCO (4.61 g at 97% w/w, 0.04 mols) was added, followed by isopropyl acetate (30.9 g) and then, after 10 minutes, 2-cyanophenol (12.2 g at 97.5% w/w, 0.1 mols) was charged. The reaction was held at 40° C. for 105 minutes at which time GC analysis showed that 62% by area of methyl(E)-2-{2-[6-chloropyrimidin-4-yloxy]phenyl}-3-methoxyacrylate remained. After stirring at ambient temperature for 16 hours and then at 40° C. for 105 minutes the reaction had stopped. A further charge of potassium carbonate was made (7.04 g at 98% w/w, 0.05 mols) and stirring continued for 160 minutes, with very little further reaction taking place. GC analysis showed that 40 area % methyl(E)-2-{2-[6-chloropyrimidin-4-yloxy]phenyl}-3-methoxyacrylate remained.

o) Coupling of methyl(E)-2-{2-[6-chloropyrimidin-4-yloxy]phenyl}-3-methoxyacrylate with 2-cyanophenol in cyclohexanone with 2.5 mol % DABCO added after 2-cyanophenol but before methyl(E)-2-{2-[6-chloropyrimidin-4-yloxy]phenyl}-3-methoxyacrylate Cyclohexanone (198.2 g) was heated to 100° C., with stirring, and 2-cyanophenol (24.4 g at 97.5% w/w, 0.2 mols) was added. After 10 minutes potassium carbonate (70.4 g at 98% w/w, 0.5 mols) was added. The mixture was stirred for 10 minutes during which time frothing and gassing was observed. DABCO (0.289 g at 97% w/w, 0.0025 mols) and methyl(E)-2-{2-[6-chloropyrimidin-4-yloxy]phenyl}-3-methoxyacrylate (32.8 g at 98% w/w, 0.1 mols) were then added at 10 minute intervals. The reaction was stirred at 100° C. for 80 minutes. The temperature was adjusted to 80° C. and hot water (106.2 g) was added keeping the temperature above 70° C. The mixture was stirred at 75° C. for 30 minutes, and then settled and the aqueous phase separated. The cyclohexanone solution (255.3 g) contained methyl(E)-2-{2-[6-(2-cyanophenoxy)pyrimidin-4-yloxy]phenyl}-3-methoxyacrylate (15.2% w/w), 96.3% of theory.

p) Coupling of methyl(E)-2-{2-[6-chloropyrimidin-4-yloxy]phenyl}-3-methoxyacrylate with 2-cyanophenol in cyclohexanone with 2.5 mol % DABCO added before 2-cyanophenol but after methyl(E)-2-{2-[6-chloropyrimidin-4-yloxy]phenyl}-3-methoxyacrylate Cyclohexanone (198.2 g) was heated to 100° C., with stirring, and methyl (E)-2-{2-[6-chloropyrimidin-4-yloxy]phenyl}-3-methoxyacrylate (32.8 g at 98% w/w, 0.1 mols) was added. After stirring for 10 minutes DABCO (0.289 g at 97% w/w, 0.0025 mols) was introduced and stirring continued for 10 minutes before adding potassium carbonate (70.4 g at 98% w/w, 0.5 mols). After stirring for a further 10 minutes at 100° C., 2-cyanophenol (24.4 g at 97.5% w/w, 0.2 mols) was added. The reaction was stirred at 100° C. for 15 hours. The temperature was adjusted to 80° C. and hot water (106.2 g) was added keeping the temperature above 70° C. The mixture was stirred at 75° C. for 30 minutes, and then settled and the aqueous phase separated. The cyclohexanone solution (256.5 g) contained methyl(E)-2-{2-[6-(2-cyanophenoxy)pyrimidin-4-yloxy]phenyl}-3-methoxyacrylate (11.8% w/w), 75.1% of theory.

q) Coupling of methyl(E)-2-{2-[6-chloropyrimidin-4-yloxy]phenyl}-3-methoxyacrylate with 2-cyanophenol in toluene with 10 mol % DABCO added after 2-cyanophenol and with DBU as the base Toluene (40.8 g) was stirred and heated to 70° C. DABCO (0.85 g at 98% w/w, 0.007 mols) and 2-cyanophenol (9.9 g at 97.5% w/w, 0.08 mols) were added at 10 minute intervals. After a further 10 minutes DBU (13.8 g at 98% w/w, 0.09 mols) was added over 5 minutes (exotherm to 74° C.). After stirring for a further 10 minutes, methyl(E)-2-{2-[6-chloropyrimidin-4-yloxy]phenyl}-3-methoxyacrylate (24.2 g at 98% w/w, 0.074 mols) was added and the reaction stirred at 70° C. for 60 minutes (reaction was complete in 30 minutes). Hot water (75° C.) (78.3 g) was added and the mixture stirred for 15 minutes at 70-75° C., then settled and the aqueous phase separated. A second water wash (78.3 g) was applied in the same way. The toluene phase (73.1 g) contained methyl (E)-2-{2-[6-(2-cyanophenoxy)pyrimidin-4-yloxy]phenyl}-3-methoxyacrylate (38.6% w/w), 94.7% of theory.

r) Coupling of methyl(E)-2-{2-[6-chloropyrimidin-4-yloxy]phenyl}-3-methoxyacrylate with 2-cyanophenol in toluene with 10 mol % DABCO added before 2-cyanophenol and with DBU as the base Toluene (40.8 g) was stirred and heated to 70° C. Methyl (E)-2-{2-[6-chloropyrimidin-4-yloxy]phenyl}-3-methoxyacrylate (24.2 g at 98% w/w, 0.074 mols), DABCO (0.85 g at 98% w/w, 0.007 mols) and 2-cyanophenol (9.9 g at 97.5% w/w, 0.08 mols) were added at 10 minute intervals, maintaining the temperature at 70° C. After a further 10 minutes DBU (13.8 g at 98% w/w, 0.09 mols) was added over 5.5 minutes. During the addition the temperature went up to 78° C. and cooling was applied to maintain 70° C. The reaction mixture was stirred at 70° C. for 90 minutes (still 35.8 area % methyl (E) -2-{2-[6-chloropyrimidin-4-yloxy]phenyl}-3-methoxyacrylate unreacted by GC analysis). The reaction temperature was raised to 80° C. and stirring continued for another 90 minutes at which time the reaction was still not complete (14.2 area % methyl(E)-2-{2-[6-chloropyrimidin-4-yloxy]phenyl}-3-methoxyacrylate unreacted by GC analysis). The temperature was raised to 100° C. and stirring continued for a further 60 minutes to complete the reaction. The reaction mixture was cooled to 70° C. before hot water (75° C.) (78.3 g) was added. The mixture was stirred for 15 minutes at 70-75° C., then settled and the aqueous phase separated. A second water wash (78.3 g) was applied in the same way. The toluene phase (66.6 g) contained methyl (E)-2-{2-[6-(2-cyanophenoxy)pyrimidin-4-yloxy]phenyl}-3-methoxyacrylate (32.8% w/w), 73.3% of theory.

It can be seen from the results above that, in all cases, where the DABCO is mixed with the compound of formula II in the absence of 2-cyanophenol, the yield of product is decreased and often the reaction time is increased when compared to a reaction carried out under the same conditions but wherein the DABCO is not mixed with the compound of formula II in the absence of 2-cyanophenol. Compare, for instance, example (a) with any of (b), (c) and (d); example (f) with (e); examples (h) and (k) with any of (g), (i) and (j); example (m) with (l); example (p) with (O); and example (r) with (q). In addition, the benefits of controlling the reaction conditions to physically prevent DABCO and the compound of formula II reacting can also be seen. Compare, for example, (m) in which, although DABCO is added to the compound of formula II in the absence of 2-cyanophenol, it is only able to react slowly with the compound of formula II due to the low solubility of the system, with (n) in which the solubility has been increased: in the latter, a significant proportion of the starting material is unreacted after more than 16 hours.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as is each individual publication were specifically and individually indicated to so incorporated by reference.

The invention claimed is:
1. A process for preparing a compound of formula (I):

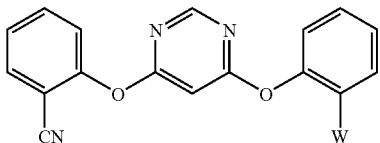

which comprises either
(a) reacting a compound of formula (II):

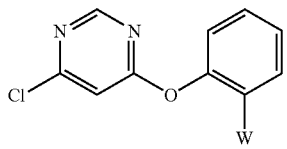

with 2-cyanophenol, or a salt thereof, in the presence of between 0.1 and 40 mol % of 1,4-diazabicyclo[2.2.2] octane, or
(b) reacting a compound of the formula (III):

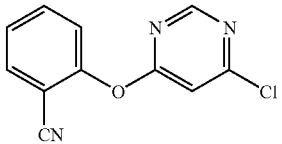

with a compound of the formula (IV):

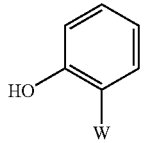

or a salt thereof, in the presence of between 0.1 and 40 mol % of 1,4-diazabicyclo[2.2.2]octane;
wherein W is the methyl(E)-2-(3-methoxy)acrylate group $C(CO_2CH_3)$=$CHOCH_3$ or the methyl 2-(3,3-dimethoxy)propanoate group $C(CO_2CH_3)CH(OCH_3)_2$, and wherein 1,4-diazabicyclo[2.2.2]octane is not mixed with the compound of formula (II) or the compound of formula (III) unless 2-cyanophenol or the compound of formula (IV) is present; or (ii) 1,4-diazabicyclo[2.2.2] octane is present as an acid salt or (iii) conditions are such that 1,4-diazabicyclo[2.2.2]octane and the compound of formula (II) or the compound of formula (III) are not able to react with each other; with the proviso that when between 0.1 and 2 mol % 1,4-diazabicyclo[2.2.2] octane is used, the 1,4-diazabicyclo[2.2.2]octane is not added last.

2. The process according to claim 1 which is carried out in the presence of between 0.5 and 5 mol % of 1,4-diazabicyclo [2.2.2]octane.

3. The process according to claim 1 which is carried out in an inert solvent or diluent.

4. The process according to claim 3 in which the inert solvent or diluent is methyl isobutyl ketone, cyclohexanone, N,N-diisopropylethylamine, toluene, isopropyl acetate or N,N-dimethylformamide.

5. The process according to claim 4 in which the inert solvent or diluent is N,N-dimethylformamide.

6. The process according to claim 1 which is carried out in an aqueous organic solvent system.

7. The process according to claim 6, wherein the organic solvent is cyclohexanone, methyl isobutyl ketone, isopropyl acetate, or N,N-dimethylformamide.

8. The process according to claim 6 wherein, as a salt of 2-cyanophenol, potassium 2-cyanophenoxide is used.

9. The process according to claim 1 which is carried out in the presence of an acid acceptor.

10. The process according to claim 9 in which the acid acceptor is potassium carbonate or sodium carbonate.

11. The process according to claim 1 which is carried out at a temperature of from 0 to 120° C.

* * * * *